United States Patent
Lo et al.

(10) Patent No.: US 9,579,106 B2
(45) Date of Patent: Feb. 28, 2017

(54) SHOULDER ARTHROPLASTY INSTRUMENTATION

(75) Inventors: Darrick Lo, Green Brook, NJ (US); Joseph Lipman, New York, NY (US); Andrew D. Pearle, Rye, NY (US)

(73) Assignee: NEW YORK SOCIETY FOR THE RELIEF OF THE RUPTURED AND CRIPPLED, MAINTAINING THE HOSPITAL FOR SPECIAL SURGERY, New York, NY (US)

( * ) Notice: Subject to any disclaimer, the term of this patent is extended or adjusted under 35 U.S.C. 154(b) by 453 days.

(21) Appl. No.: 13/075,378

(22) Filed: Mar. 30, 2011

(65) Prior Publication Data

US 2012/0078258 A1    Mar. 29, 2012

Related U.S. Application Data

(60) Provisional application No. 61/319,484, filed on Mar. 31, 2010, provisional application No. 61/325,435, filed on Apr. 19, 2010.

(51) Int. Cl.
  *A61B 17/56* (2006.01)
  *A61B 17/15* (2006.01)
  *A61B 17/17* (2006.01)

(52) U.S. Cl.
  CPC ...... *A61B 17/15* (2013.01); *A61B 2017/1778* (2013.01); *A61B 2017/568* (2013.01); *A61B 2034/108* (2016.02)

(58) Field of Classification Search
  CPC ............ A61B 17/15; A61B 2017/1778; A61B 2017/568; A61B 2019/508; A61B 2034/108
  USPC .............. 606/86 R, 87–90, 96–98, 102, 104; 623/19.11–19.14
  See application file for complete search history.

(56) References Cited

U.S. PATENT DOCUMENTS

| | | | |
|---|---|---|---|
| 4,986,833 A * | 1/1991 | Worland | 623/19.11 |
| 5,030,219 A | 7/1991 | Matsen, III et al. | |
| 5,098,383 A | 3/1992 | Hemmy et al. | |
| 5,141,680 A | 8/1992 | Almquist et al. | |
| 5,768,134 A | 6/1998 | Swaelens | |
| 5,769,856 A | 6/1998 | Dong et al. | |
| 5,800,551 A * | 9/1998 | Williamson et al. | 623/19.11 |
| 6,327,491 B1 | 12/2001 | Franklin et al. | |
| 6,364,910 B1 * | 4/2002 | Shultz et al. | 623/19.13 |
| 6,712,856 B1 | 3/2004 | Carignan et al. | |
| 6,772,026 B2 | 8/2004 | Bradbury et al. | |
| 6,827,723 B2 | 12/2004 | Carson | |
| 7,194,120 B2 | 3/2007 | Wicker et al. | |
| 7,534,263 B2 | 5/2009 | Burdulis, Jr. et al. | |

(Continued)

FOREIGN PATENT DOCUMENTS

| | | |
|---|---|---|
| EP | 0558789 A1 | 9/1993 |
| EP | 1639949 A1 | 3/2006 |

(Continued)

OTHER PUBLICATIONS

US 8,849,621, 09/2014, Fitz et al. (withdrawn)

(Continued)

*Primary Examiner* — Eduardo C Robert
*Assistant Examiner* — Marcela I Shirsat
(74) *Attorney, Agent, or Firm* — Shay Glenn LLP

(57) ABSTRACT

Patient specific shoulder component implant instruments are described for hemi and total, normal and reverse shoulder arthroplasty.

10 Claims, 11 Drawing Sheets

(56) References Cited

U.S. PATENT DOCUMENTS

| | | |
|---|---|---|
| 7,618,451 B2 | 11/2009 | Berez et al. |
| 7,695,477 B2 | 4/2010 | Creger et al. |
| 7,799,077 B2 | 9/2010 | Lang et al. |
| 8,092,465 B2 | 1/2012 | Metzger |
| 8,241,293 B2 * | 8/2012 | Stone et al. .................. 606/87 |
| 8,282,646 B2 | 10/2012 | Schoenefeld |
| 8,382,765 B2 | 2/2013 | Axelson et al. |
| 8,480,679 B2 | 7/2013 | Park et al. |
| 8,617,171 B2 | 12/2013 | Park et al. |
| 8,632,547 B2 | 1/2014 | Maxson et al. |
| 8,644,973 B2 | 2/2014 | Bake et al. |
| 8,655,468 B2 | 2/2014 | Bake et al. |
| 8,657,822 B2 | 2/2014 | Bake et al. |
| 8,682,052 B2 | 3/2014 | Fitz et al. |
| 8,715,291 B2 | 5/2014 | Park et al. |
| 8,735,773 B2 | 5/2014 | Lang |
| 8,764,760 B2 | 7/2014 | Metzger et al. |
| 8,808,301 B1 | 8/2014 | Nofsinger |
| 8,828,012 B2 | 9/2014 | May et al. |
| 8,882,770 B2 | 11/2014 | Barsoum |
| 8,965,088 B2 | 2/2015 | Tsougarakis et al. |
| 8,986,309 B1 | 3/2015 | Murphy |
| 9,017,336 B2 | 4/2015 | Park et al. |
| 9,020,788 B2 | 4/2015 | Lang et al. |
| 9,254,155 B2 | 2/2016 | Iannotti et al. |
| 9,381,025 B2 | 7/2016 | Fitz et al. |
| 2005/0107799 A1 | 5/2005 | Graf et al. |
| 2005/0148843 A1 | 7/2005 | Roose |
| 2005/0203528 A1 | 9/2005 | Couture |
| 2006/0079963 A1 * | 4/2006 | Hansen .................. 623/19.11 |
| 2007/0172815 A1 | 7/2007 | Weaver |
| 2007/0198022 A1 | 8/2007 | Lang et al. |
| 2007/0233121 A1 | 10/2007 | Carson et al. |
| 2007/0239282 A1 | 10/2007 | Caylor et al. |
| 2007/0250174 A1 | 10/2007 | Tornier et al. |
| 2007/0276501 A1 | 11/2007 | Betz et al. |
| 2008/0114370 A1 | 5/2008 | Schoenefeld |
| 2008/0215059 A1 | 9/2008 | Carignan et al. |
| 2008/0243127 A1 * | 10/2008 | Lang et al. .................. 606/87 |
| 2008/0255566 A1 | 10/2008 | Lyons |
| 2008/0269906 A1 | 10/2008 | Iannotti et al. |
| 2008/0287954 A1 | 11/2008 | Kunz et al. |
| 2008/0319491 A1 | 12/2008 | Schoenefeld |
| 2009/0018546 A1 | 1/2009 | Daley |
| 2009/0088763 A1 | 4/2009 | Aram et al. |
| 2009/0131941 A1 | 5/2009 | Park et al. |
| 2009/0138020 A1 | 5/2009 | Park et al. |
| 2009/0151736 A1 | 6/2009 | Belcher et al. |
| 2009/0163922 A1 | 6/2009 | Meridew et al. |
| 2009/0222016 A1 | 9/2009 | Park et al. |
| 2009/0254093 A1 | 10/2009 | White et al. |
| 2009/0274350 A1 | 11/2009 | Pavlovskaia et al. |
| 2010/0009314 A1 | 1/2010 | Tardieu |
| 2010/0023015 A1 | 1/2010 | Park |
| 2010/0030231 A1 | 2/2010 | Revie et al. |
| 2010/0049195 A1 | 2/2010 | Park et al. |
| 2010/0082035 A1 | 4/2010 | Keefer |
| 2010/0087829 A1 | 4/2010 | Metzger et al. |
| 2010/0152741 A1 | 6/2010 | Park et al. |
| 2010/0152782 A1 | 6/2010 | Stone et al. |
| 2010/0191242 A1 | 7/2010 | Massoud |
| 2010/0217270 A1 | 8/2010 | Polinski et al. |
| 2010/0256479 A1 | 10/2010 | Park et al. |
| 2010/0274253 A1 | 10/2010 | Ure |
| 2010/0286700 A1 | 11/2010 | Snider et al. |
| 2010/0292743 A1 | 11/2010 | Singhal et al. |
| 2010/0322497 A1 | 12/2010 | Dempsey |
| 2011/0015636 A1 | 1/2011 | Katrana et al. |
| 2011/0015639 A1 | 1/2011 | Metzger et al. |
| 2011/0029088 A1 * | 2/2011 | Rauscher et al. .......... 623/19.11 |
| 2011/0046735 A1 | 2/2011 | Metzger et al. |
| 2011/0054478 A1 | 3/2011 | Vanasse et al. |
| 2011/0060417 A1 | 3/2011 | Simmen et al. |
| 2011/0071533 A1 | 3/2011 | Metzger et al. |
| 2011/0092804 A1 | 4/2011 | Schoenefeld et al. |
| 2011/0092977 A1 | 4/2011 | Salehi et al. |
| 2011/0144760 A1 | 6/2011 | Wong et al. |
| 2011/0160736 A1 | 6/2011 | Meridew et al. |
| 2011/0172672 A1 | 7/2011 | Dubeau et al. |
| 2011/0184419 A1 | 7/2011 | Meridew et al. |
| 2011/0190775 A1 | 8/2011 | Ure |
| 2011/0190899 A1 | 8/2011 | Pierce et al. |
| 2011/0213372 A1 | 9/2011 | Keefer et al. |
| 2011/0218545 A1 | 9/2011 | Catanzarite et al. |
| 2012/0010711 A1 | 1/2012 | Antonyshyn et al. |
| 2012/0078259 A1 | 3/2012 | Meridew |
| 2012/0109137 A1 | 5/2012 | Iannotti et al. |
| 2012/0123420 A1 | 5/2012 | Honiball |
| 2012/0130382 A1 | 5/2012 | Iannotti et al. |
| 2012/0141034 A1 | 6/2012 | Iannotti et al. |
| 2012/0143267 A1 * | 6/2012 | Iannotti et al. ............. 606/86 R |
| 2012/0203233 A1 | 8/2012 | Yoshida et al. |
| 2012/0209276 A1 | 8/2012 | Schuster |
| 2012/0226283 A1 | 9/2012 | Meridew et al. |
| 2012/0234329 A1 | 9/2012 | Vancraen et al. |
| 2012/0245647 A1 | 9/2012 | Kunz et al. |
| 2012/0245699 A1 | 9/2012 | Lang et al. |
| 2012/0259335 A1 | 10/2012 | Scifert et al. |
| 2012/0271366 A1 | 10/2012 | Katrana et al. |
| 2012/0276509 A1 | 11/2012 | Iannotti et al. |
| 2012/0289965 A1 | 11/2012 | Gelaude et al. |
| 2012/0303004 A1 | 11/2012 | Uthgenannt et al. |
| 2012/0316564 A1 | 12/2012 | Serbousek et al. |
| 2012/0323246 A1 | 12/2012 | Catanzarite et al. |
| 2013/0001121 A1 | 1/2013 | Metzger |
| 2013/0018378 A1 * | 1/2013 | Hananouchi .......... A61B 90/11 606/87 |
| 2013/0053854 A1 | 2/2013 | Schoenefeld et al. |
| 2013/0066321 A1 | 3/2013 | Mannss et al. |
| 2013/0085500 A1 | 4/2013 | Meridew et al. |
| 2013/0110116 A1 * | 5/2013 | Kehres .............. A61B 17/1739 606/96 |
| 2013/0110470 A1 | 5/2013 | Vanasse |
| 2013/0116699 A1 | 5/2013 | Smith et al. |
| 2013/0119579 A1 | 5/2013 | Iannotti et al. |
| 2013/0123850 A1 | 5/2013 | Schoenefeld et al. |
| 2013/0138111 A1 | 5/2013 | Aram et al. |
| 2013/0158671 A1 | 6/2013 | Uthgenannt et al. |
| 2013/0197528 A1 | 8/2013 | Zakaria et al. |
| 2013/0197529 A1 | 8/2013 | Metzger et al. |
| 2013/0204384 A1 | 8/2013 | Hensley et al. |
| 2013/0230838 A1 | 9/2013 | Iannotti et al. |
| 2013/0261503 A1 | 10/2013 | Sherman et al. |
| 2013/0282132 A1 | 10/2013 | White et al. |
| 2013/0317510 A1 | 11/2013 | Couture et al. |
| 2013/0338673 A1 * | 12/2013 | Keppler .............. A61B 17/1739 606/96 |
| 2014/0012266 A1 * | 1/2014 | Bonin, Jr. ............. A61B 17/15 606/88 |
| 2014/0018934 A1 | 1/2014 | Meridew et al. |
| 2014/0052270 A1 | 2/2014 | Witt et al. |
| 2014/0066720 A1 | 3/2014 | Wilkinson et al. |
| 2014/0066938 A1 | 3/2014 | Catanzarite et al. |
| 2014/0081342 A1 | 3/2014 | Iannotti et al. |
| 2014/0088724 A1 | 3/2014 | Meridew |
| 2014/0094814 A1 | 4/2014 | Hughes et al. |
| 2014/0094816 A1 | 4/2014 | White et al. |
| 2014/0100578 A1 | 4/2014 | Metzger et al. |
| 2014/0107654 A1 | 4/2014 | Kehres et al. |
| 2014/0107715 A1 | 4/2014 | Heilman et al. |
| 2014/0114320 A1 | 4/2014 | Kurtz |
| 2014/0135940 A1 | 5/2014 | Goldstein et al. |
| 2014/0163564 A1 | 6/2014 | Bollinger |
| 2014/0163565 A1 | 6/2014 | Bollinger |
| 2014/0188119 A1 | 7/2014 | Catanzarite et al. |
| 2014/0243833 A1 | 8/2014 | Smith |
| 2014/0257304 A1 | 9/2014 | Eash |
| 2014/0276854 A1 | 9/2014 | Schoenefeld et al. |
| 2014/0276856 A1 | 9/2014 | Schoenefeld |
| 2014/0276870 A1 | 9/2014 | Eash |
| 2014/0276873 A1 | 9/2014 | Meridew et al. |
| 2014/0316416 A1 | 10/2014 | Liu et al. |
| 2014/0324058 A1 | 10/2014 | Metzger et al. |
| 2014/0378979 A1 | 12/2014 | Stone et al. |

(56) References Cited

U.S. PATENT DOCUMENTS

| | | |
|---|---|---|
| 2015/0088142 A1 | 3/2015 | Gibson |
| 2015/0088143 A1 | 3/2015 | Lipman et al. |
| 2015/0088293 A1 | 3/2015 | Metzger |
| 2015/0112348 A1 | 4/2015 | Schoenefeld et al. |
| 2015/0112349 A1 | 4/2015 | Schoenefeld |
| 2015/0150688 A1 | 6/2015 | Vanasse et al. |
| 2015/0223941 A1 | 8/2015 | Lang |
| 2015/0305752 A1 | 10/2015 | Eash |
| 2015/0320430 A1 | 11/2015 | Kehres et al. |
| 2015/0342620 A1 | 12/2015 | Winslow |
| 2015/0342622 A1 | 12/2015 | Kehres et al. |
| 2015/0351778 A1 | 12/2015 | Uthgenannt et al. |
| 2016/0008009 A1 | 1/2016 | Aram et al. |
| 2016/0074052 A1 | 3/2016 | Keppler et al. |
| 2016/0089163 A1 | 3/2016 | Eash et al. |
| 2016/0089166 A1 | 3/2016 | Maxson |
| 2016/0095608 A1 | 4/2016 | Iannotti et al. |
| 2016/0100847 A1 | 4/2016 | Maxson |
| 2016/0120555 A1 | 5/2016 | Bonin, Jr. et al. |
| 2016/0143744 A1 | 5/2016 | Bojarski et al. |
| 2016/0206331 A1 | 7/2016 | Fitz et al. |

FOREIGN PATENT DOCUMENTS

| | | | |
|---|---|---|---|
| WO | WO97/29901 A1 | 8/1997 | |
| WO | WO02/11945 A1 | 2/2002 | |
| WO | WO2009/058319 A1 | 5/2009 | |
| WO | WO2010/121147 A1 | 10/2010 | |
| WO | WO2011/056995 A2 | 5/2011 | |
| WO | WO2011/075697 A2 | 6/2011 | |
| WO | 2013060851 | 5/2013 | |
| WO | 2013062851 | 5/2013 | |
| WO | WO2015/071757 A1 | 5/2015 | |

OTHER PUBLICATIONS

R.Sean Churchill, John J. Brems, Helmuth Kotschic, Glenoid size, inclination, and version: An anatomic study, Journal of Shoulder and Elbow Surgery, vol. 10, Issue 4, Jul.-Aug. 2001, pp. 327-332, ISSN 1058-2746, http://www.sciencedirect.com/science/article/pii/S1058274601551629. last accessed on Nov. 13, 2014.*
Boileau, P., Walch, G.; The Three-Dimensional Geometry of the Proximal Humerus, 1997 British Editorial Society of Bone and Joint Surgery, vol. 79-B, No. 5, Sep. 1997.
Krishnam, S.P., Dawood, A, Richards, R., Henckel, J., and Hart, A.J., A Review of Rapid Prototyped Surgical Guides for Patient-Specific Total Knee Replacement, The Journal of Bone & Joint Surgery, vol. 94-B, No. 11, Nov. 2012.
Iannotti et al., U.S. Appl. No. 61/408,324, filed Oct. 29, 2010, entitled "System and Method for Assisting with Attachment of a Stock Implant to a Patient Issue".
Iannotti et al., U.S. Appl. No. 61/408,376, filed Oct. 29, 2010, entitled "System and Method for Assisting with Arrangement of a Stock Instrument with Respect to a Patient Tissue".
Iannotti et al., U.S. Appl. No. 61/408,392, filed Oct. 29, 2010, entitled "System of Preoperative Planning and Provision of Patient-Specific Surgical Aids".
Murase et al., "Three-Dimensional Corrective Osteotomy of Malunited Fractures of the Upper Extremity with Use of a Computer Simulation System", The Journal of Bone & Joint Surgery, 90(11): pp. 2375-2389; Nov. 2008.
Oka et al., "Accuracy of Corrective Osteotomy Using a Custom-Designed Device Based on a Novel Computer Simulation System", Journal of Orthopaedic Science; 16(1); pp. 85-92; Jan. 2011.
Bohsali et al.; Complications of total shoulder arthroplasty; J Bone Joint Surg Am.; 88(10); pp. 2279-2292; Oct. 2006.
Bojarski et al., U.S. Appl. No. 61/443,155, filed Feb. 15, 2011, entitled "Patient-Adapted and Improved Articular Implants, Designs and Related Guide Tools".

Churchill et al.; Glenoid cementing may generate sufficient heat to endanger the surrounding bone; Clin Orthop Relat Res; (419); pp. 76-79; Feb. 2004.
Dallalana et al.; Accuracy of patient-specific instrumentation in anatomic and reverse total shoulder arthroplasty; Int J Shoulder Surg.; 10(2); pp. 59-66; Apr.-Jun. 2016.
Eraly et al.; A patient-specific guide for optimizing custom-made glenoid implantation in cases of severe glenoid defects: an in vitro study; J Shoulder Elbow Surg.; 25(5); pp. 837-845; May 2016.
Fox et al.; Survival of the glenoid component in shoulder arthroplasty; J Shoulder Elbow Surg; 18(6); pp. 859-863; Nov./Dec. 2009.
Heylen et al.; Patient-specific instrument guidance of glenoid component implantation reduces inclination variability in total and reverse shoulder arthroplasty; J Shoulder Elbow Surg.; 25(2); pp. 186-192; Feb. 2016.
Iannotti et al.; Three-Dimensional Preoperative Planning Software and a Novel Information Transfer Technology Improve Glenoid Component Positioning; J Bone Joint Surg Am.; 96(9); pp. e71(1-8); May 2014.
Levy et al.; Accuracy of patient-specific guided glenoid baseplate positioning for reverse shoulder arthroplasty; J Shoulder Elbow Surg.; 23(10); pp. 1563-1567; Oct. 2014.
Lewis et al.; Testing of a novel pin array guide for accurate three-dimensional glenoid component positioning; J Shoulder Elbow Surg.; 24(12); pp. 1939-1947; Dec. 2015.
Mannss, Jurgen; GB App. No. 1003921.2 entitled "Orthopaedic Instrument", filed Mar. 10, 2010.
Meridew et al., U.S. Appl. No. 61/446,660, filed Feb. 25, 2011, entitled "Patient-Specific Acetabular Guides and Associated Instruments".
Metzger et al., U.S. Appl. No. 60/812,694, filed Jun. 9, 2006, entitled "Patient Specific Knee Alignment Guide And Associated Method".
Metzger, U.S. Appl. No. 60/912,178, filed Apr. 17, 2007, entitled "Surgery System".
Metzger, U.S. Appl. No. 60/947,813, filed Jul. 3, 2007, entitled "Patient-Specific Alignment Method".
Metzger et al., U.S. Appl. No. 61/310,752, filed Mar. 5, 2010, entitled "Method and Apparatus for Manufacturing an Implant".
Schoenefeld et al., U.S. Appl. No. 60/892,349, filed Mar. 1, 2007, entitled "Multi-Part Custom Implant Guide".
Schoenefeld et al., U.S. Appl. No. 60/911,297, filed Apr. 12, 2007, entitled "Patient-Specific Adjustable Alignment Guide".
Schoenefeld, U.S. Appl. No. 60/953,620, filed Aug. 2, 2007, entitled "Patient Positioner Having Image Marker".
Schoenefeld, U.S. Appl. No. 60/953,637, filed Aug. 2, 2007, entitled "Patient-Specific Alignment Guide for Multiple Incisions".
Sirveaux et al.; Grammont inverted total shoulder arthroplasty in the treatment of glenohumeral osteoarthritis with massive rupture of the cuff. Results of a multicentre study of 80 shoulders; J Bone Joint Surg Br; 86(3); pp. 388-395; Apr. 2004.
Sperling et al; Minimum fifteen-year follow-up of Neer hemiarthroplasty and total shoulder arthroplasty in patients aged fifty years or younger; J Shoulder Elbow Surg; 13(6); pp. 604-613; Nov./Dec. 2004.
Stewart et al.; Total shoulder replacement in rheumatoid disease; J Bone Joint Surg Br.;•, 79; pp. 68-72; Jan. 1997.
Suero et al.; Use of custom alignment guide to improve glenoid component position in total shoulder arthroplasty; Knee Surg Sports Traumatol Arthrosc; 21(12); pp. 2860-2866; (online: Aug. 30, 2012) Dec. 2013.
Torchia et al.; Total shoulder arthroplasty with the Neer prosthesis: long-term results; J Shoulder Elbow Surg; 6(6); pp. 495-505; Nov./Dec. 1997.
Walch et al.; Three-dimensional planning and use of patient-specific guides improve glenoid component position: an in vitro study; J Shoulder Elbow Surg.; 24(2); pp. 302-309; Feb. 2015.

* cited by examiner

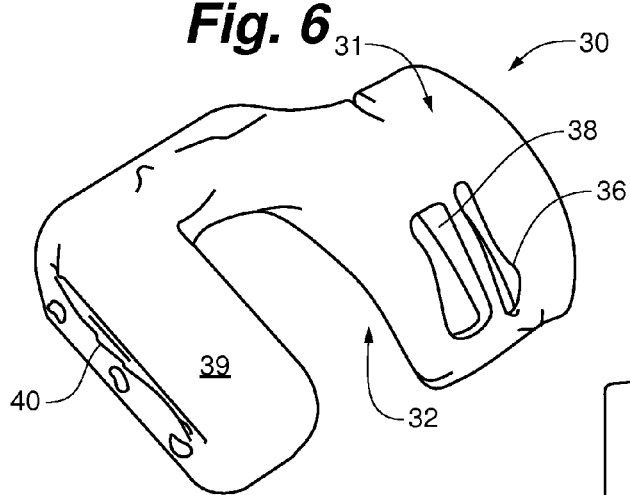
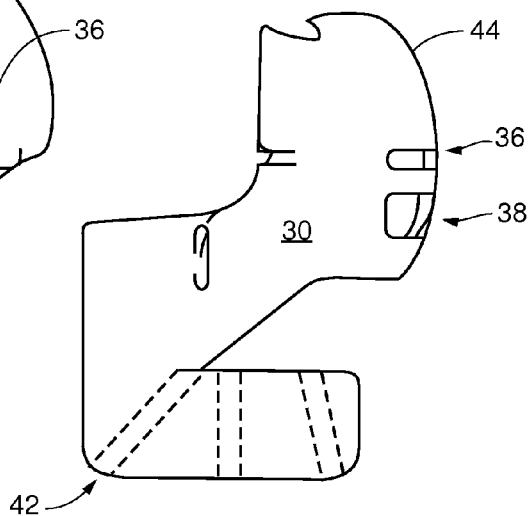
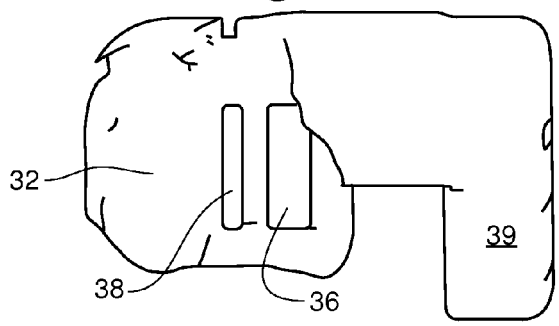
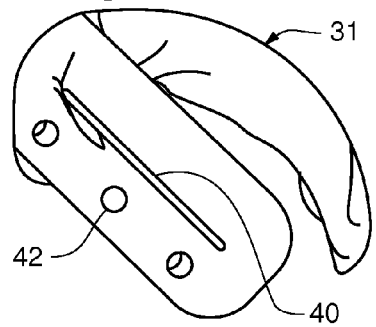
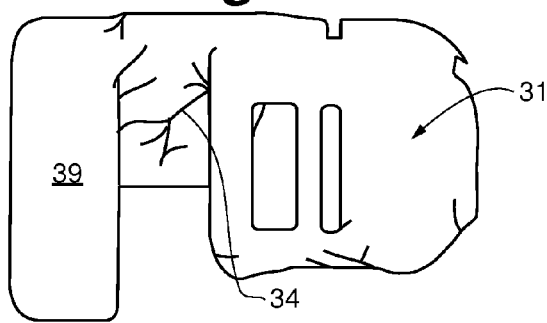

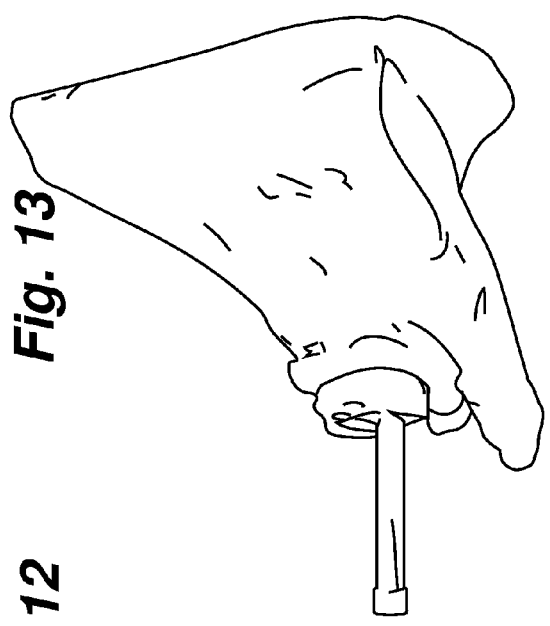
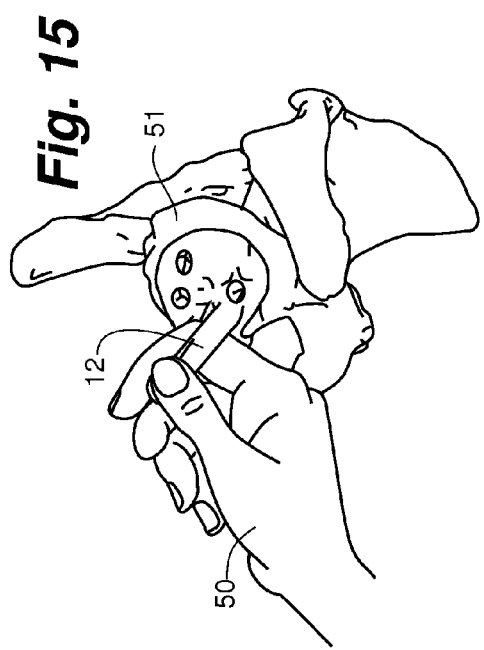
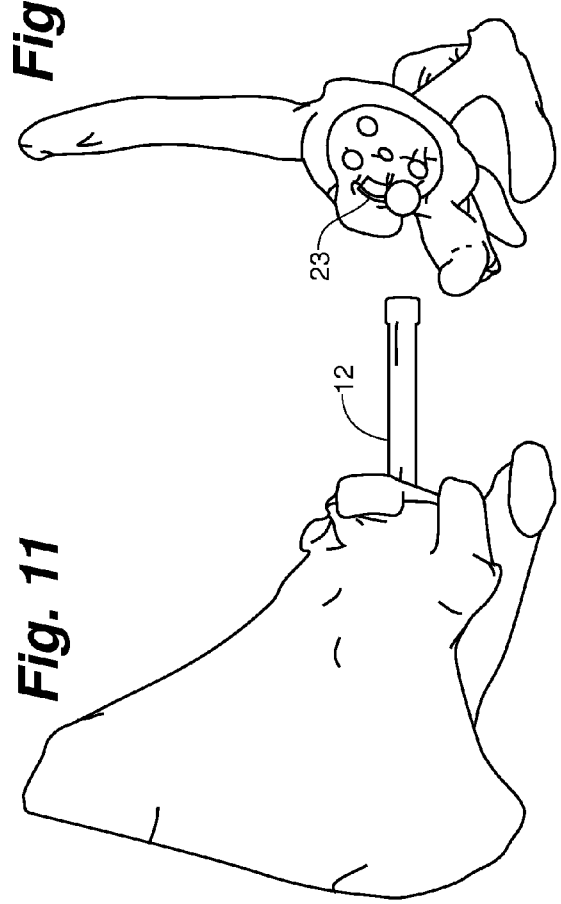
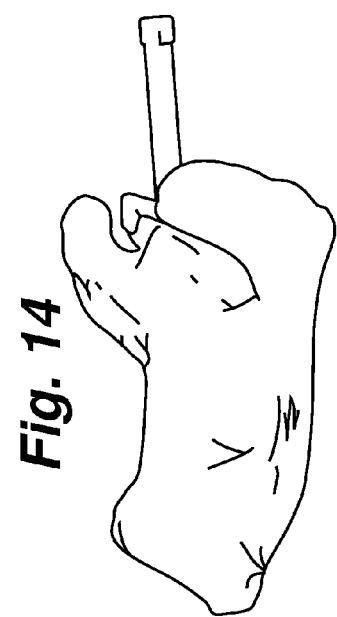

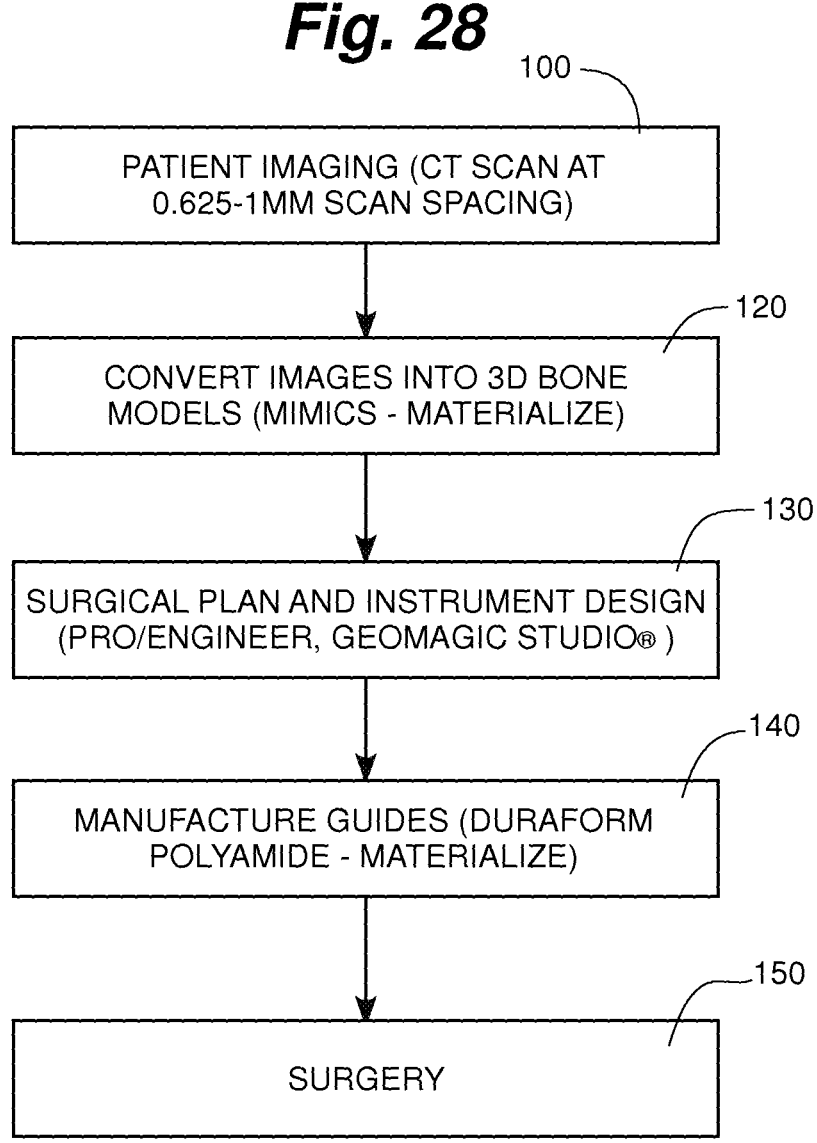

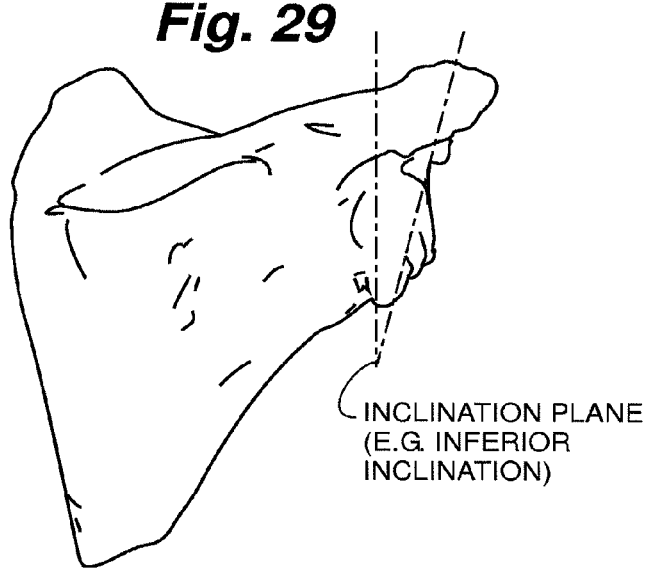
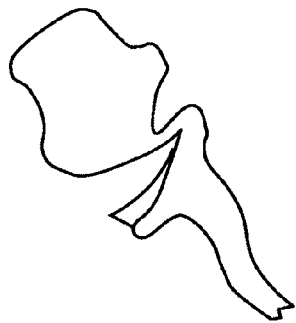
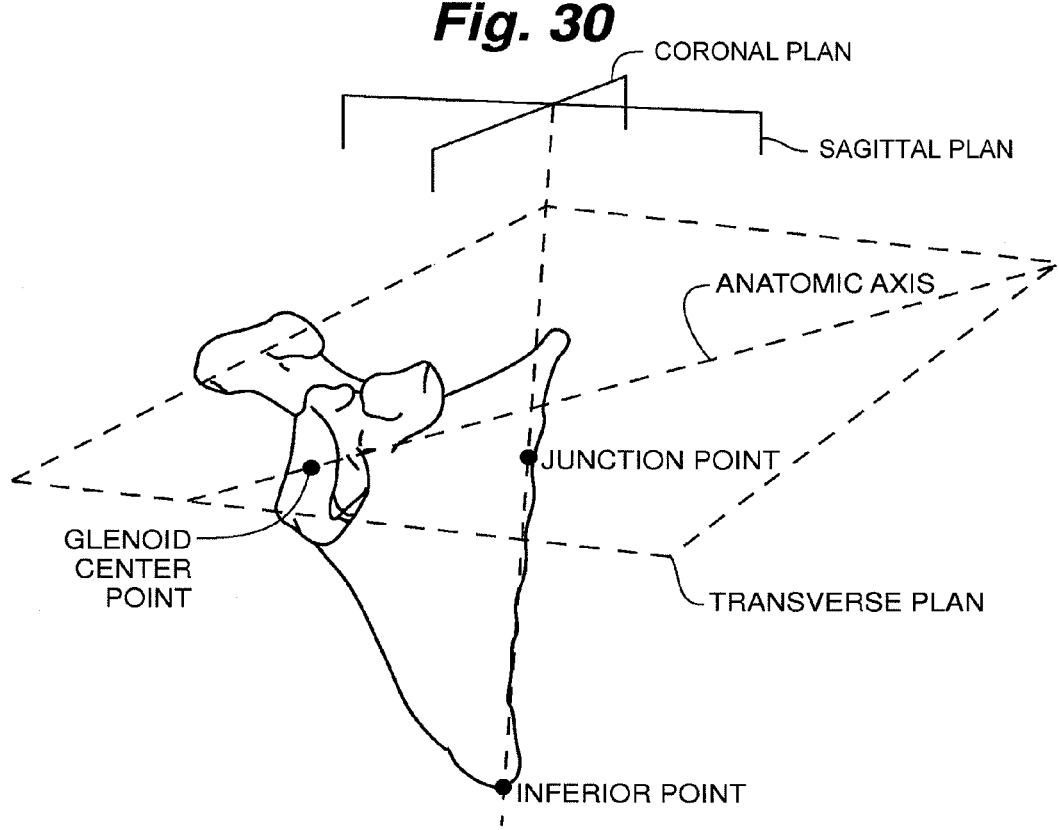

220 — VERSION PLANE (E.G. RETROVERTED GLENOID)

DTM4
DTM3
DTM2
DTM1

SHOULDER ARTHROPLASTY INSTRUMENTATION

CROSS-REFERENCE TO RELATED CASES

The present case claims the benefit of and incorporates by reference both U.S. Provisional Patent Application 61/319,484, filed Mar. 31, 2010 entitled "Patient Specific Instruments" and U.S. Provisional Patent Application 61/325,435, filed Apr. 19, 2010 entitled "Total Shoulder Arthroplasty Instrumentation".

FIELD OF THE INVENTION

The present invention relates to patient specific instrumentation to facilitate implantation of a total shoulder joint and to the process and technique for creating the instruments.

BACKGROUND OF THE INVENTION

Shoulder hemiarthroplasty is commonly used to treat patients with glenohumeral joint arthrosis. Total shoulder arthroplasty may be indicated for patients without a good articular surface on the glenoid at the time of surgery. For patients with glenohumeral joint arthrosis and an additional deficient rotator cuff, reverse total shoulder arthroplasty may be indicated. The 12%, 15%, and 22% revision rates, respectively, remains high compared to hip and knee arthroplasty. Glenoid component loosening and instability are important complications and may be caused by poor positioning of the component. An accurate placement of the complementary humeral cut is also important to achieve a stable joint.

There is a continuing need to improve the instruments used to facilitate the implantation of total shoulder joint components.

SUMMARY OF THE INVENTION

Patient specific instruments according to the invention carry surfaces and features that facilitate implantation of shoulder implant components. These surfaces are patient specific and they conform to the actual diseased joint surfaces presented by the patient. In use the physician uses the instruments to align and direct surgical cuts, to prepare the patient to receive an otherwise standard and conventional joint components of either "normal" or "reverse" configurations.

The process of the invention that results in the creation of a set of patient specific instruments takes a computed tomographic (CT) or magnetic resonance imaging (MRI) file of the patient's shoulder and presents it to a user on a computer screen. The user using a mouse or other pointing device defines reference points on the image to define geometric axes, planes and offsets. Next the user imports and aligns a computer automated design (CAD) file of the implant component with the native anatomy. The image of the implant component is merged and displayed with the anatomy image. Using a rule based system the user finds an optimum location for the glenoid component of the implant. Once the optimum location for the glenoid component is defined a custom instrument CAD file is created and a glenoid placement instrument or tool is generated from the file using conventional techniques. The tool is formed from plastic and/or metal that can be sterilized and used directly in the surgery.

In general the glenoid instrument consists of an oval or egg shaped "disk" with a protruding stalk like "handle". The disk has an upper surface and a lower surface, and a side wall separating the two.

In general the humeral instrument consists of a "cap" like structure connected to an offset "block" feature. There is a clearance volume between the "cap" and "block". The cap has an inner surface and an outer surface.

With the glenoid instrument defined and created a companion humeral cutting instrument is generated to guide the resection of bone in preparation for the implantation of the humeral component of the total shoulder implant system. The humeral instrument is likewise defined and manufactured from sterilizable plastic and/or metal in a process similar to the glenoid component. The instruments are used together and they share several characteristics.

The glenoid instrument has a complementary surface to a surface of the diseased joint formed in the lower surface.

The glenoid instrument has one or more index surfaces adjacent to its articular lower surface that facilitate placement of the tool during surgery.

The glenoid instrument has windows to permit visual confirmation of placement.

The glenoid instrument has a handle to assist in proper positioning of the instrument.

The glenoid instrument has holes that aid in defining the direction of screws should screw placement be pre-operatively determined.

The humeral resection guide instrument or humeral instrument has a complementary surface matching the humeral head contour on its inner surface.

The humeral resection guide instrument has one or more index surfaces adjacent to its articular inner surface of the cap portion that facilitates the placement of the tool during surgery.

The humeral resection guide instrument has an block offset from the cap that includes a saw slot that directs the use of a surgical saw to remove the humeral head.

The humeral resection guide instrument has holes that accept pins or other fasteners which connect the block portion of the humeral instrument to the proximal humerus bone.

BRIEF DESCRIPTION OF THE DRAWINGS

In the figures of the drawings like reference numerals indicate identical structure, wherein:

FIG. 6 shows the humeral component cutting block instrument;
FIG. 7 shows the humeral component cutting block instrument;
FIG. 8 shows the humeral component cutting block instrument;
FIG. 9 shows the humeral component cutting block instrument;
FIG. 10 shows the humeral component cutting block instrument;
FIG. 11 shows the glenoid instrument in use placed against the glenoid;
FIG. 12 shows the glenoid instrument in use placed against the glenoid;

FIG. 13 shows the glenoid instrument in use placed against the glenoid;

FIG. 14 shows the glenoid instrument in use placed against the glenoid;

FIG. 15 shows the glenoid instrument in use placed against the glenoid;

FIG. 28 is a flowchart of the process for making the instruments;

FIG. 29 shows anatomic geometry;

FIG. 30 shows part of a step in the process;

FIG. 31 shows part of a step in the process;

DETAILED DESCRIPTION

Glenoid Component Instrument

Figure 1:
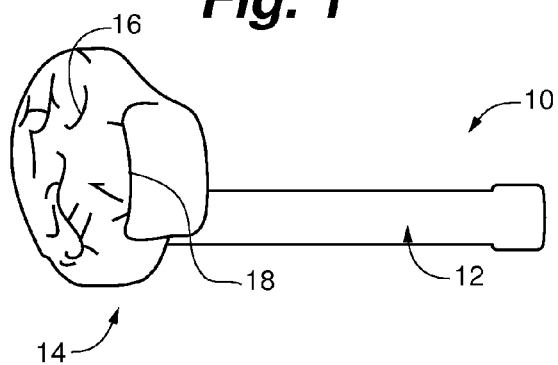
FIG. 1 is a view of the glenoid component instrument.
Figure 2:
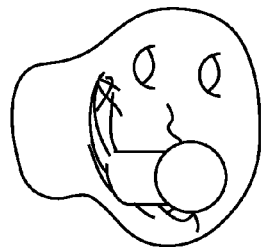
FIG. 2 is a view of the glenoid component instrument.
Figure 3:
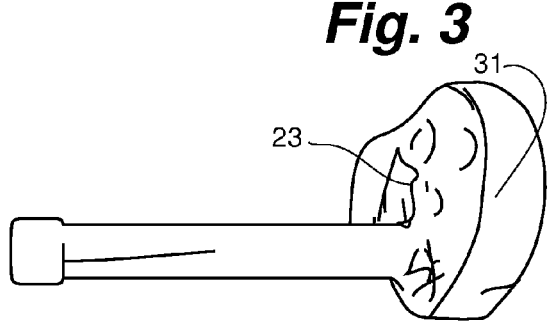
FIG. 3 is a view of the glenoid component instrument.
Figure 4:
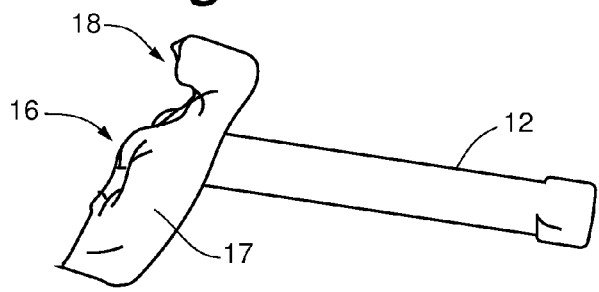
FIG. 4 is a view of the glenoid component instrument.
Figure 5:
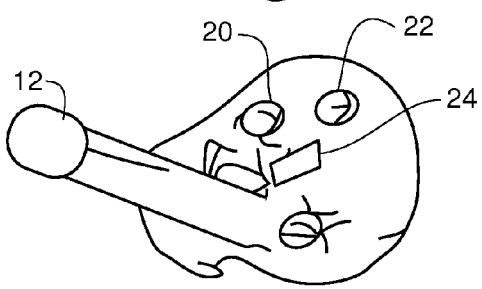
FIG. 5 is a view of the glenoid component instrument.
Figure 16:
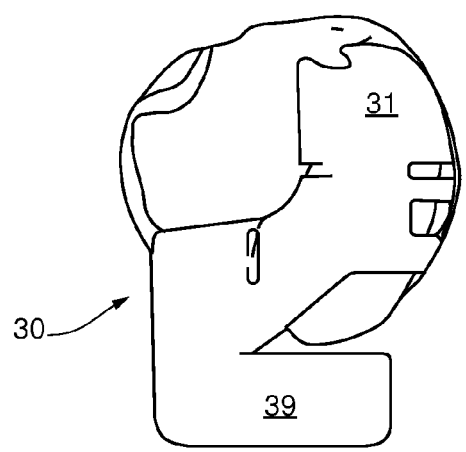
FIG. 16 shows the humeral cutting guide block in use against the humeral head.
Figure 17:
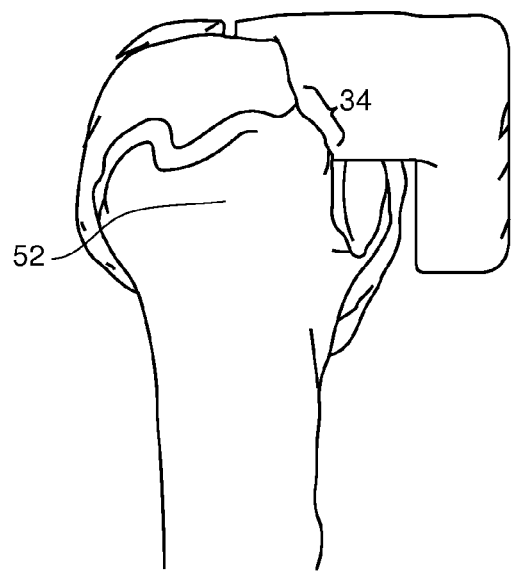
FIG. 17 shows the humeral cutting guide block in use against the humeral head.
Figure 18:
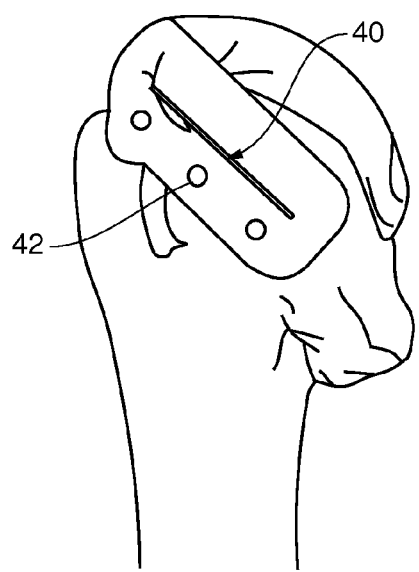
FIG. 18 shows the humeral cutting guide block in use against the humeral head.
Figure 19:
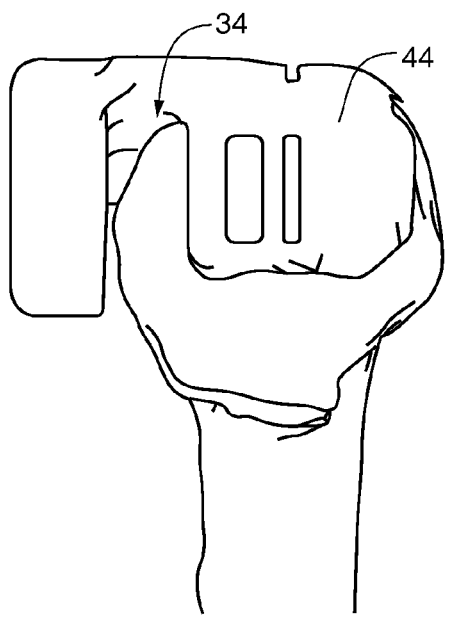
FIG. 19 shows the humeral cutting guide block in use against the humeral head.

FIG. 1 through FIG. 5 should be considered together as they show the same glenoid component instrument 10 from several different perspectives. The glenoid component instrument 10 has a handle 12 attached to a generally oval or egg shaped disk shaped instrument body 14. The disk shaped body 14 has a patient specific conformal lower surface 16 that matches the surface of the articular portion of the glenoid joint. Adjacent the patient specific bottom surface 16 is a hook like feature that matches an off articular bony portion of the glenoid. This hook 18 is also patient specific and one or more such hooks may be formed depending on the patient anatomy. These features are placed on the sidewall 17 of the disk shaped instrument body. Also present are holes passing through the disk element of the instrument body from the lower surface to the upper surface. Holes useful for directing screws or the like are seen at reference numeral 20 and 22. A hole or slot for cutting a keel slot or peg hole is seen at reference numeral 24. Additional holes acting as windows to allow visualization of the native surface are shown at reference numeral 23. Holes for bone pins can also be used to hold the glenoid instrument in place.

Humeral Component Cutting Block Instrument

FIG. 6 through FIG. 10 should be considered together as they show the same humeral component instrument from several different perspectives. The humeral component instrument 30 has a generally cap shaped element 31 with a patient specific conformal inner surface 32 that can wrap around the humeral head. There is also at least one guide surface 34 feature that is patient specific and off the articulating surface of the joint. Apertures labeled 36 and 38 in the form of windows are cut through the cap from the inner surface to the outer surface to permit visualization of the joint surface. Adjacent to cap 31 is a block feature 39 having a saw guiding slot 40 that overlies several pin holes typified by hole 42. These holes may be used to place Steinman pins or other fixation devices. There will usually be three holes at differing inclinations to rigidly attach the cutting block 30 to the bone. The block element 39 is offset from the cap 31 element by a clearance space. The fixation devices traverse this clearance space when they are pushed in to position.

Use of the Glenoid Instrument

FIG. 11 through FIG. 15 should be considered together as they show the same glenoid instrument in contact with the glenoid portion of the glenohumeral joint. Typically the physician holds the handle with his hand 50 and presses the instrument body against the joint surface 51. Tactile and visual clues that result from the patient conformal surfaces allow and facilitate registration of the instrument body with the native anatomy.

Use of the Humeral Head Cutting Block Guide

FIG. 16 through FIG. 20 should be considered together as they show the same cutting block in contact with the humeral head. In use the cap feature overlays the humeral head 52 and the conformal inner surface and index surface 34 align the instrument with the bone. Once the instrument is fastened to the bone via fixation holes 42, the saw may enter slot 40 and resect the bone. As seen best in FIG. 20 the clearance space allows the humeral instrument to accommodate muscle 37 and other tissue with minimal injury.

Glenoid Component in Position

Figure 21:
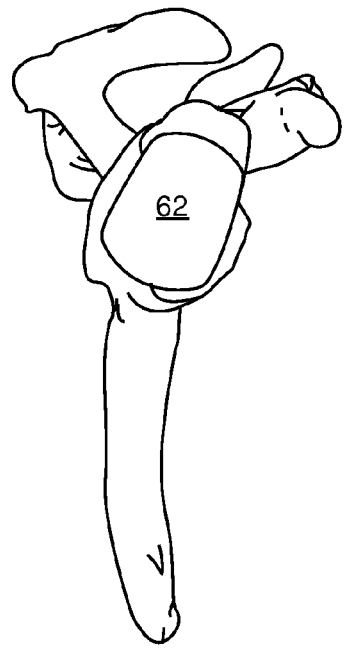
FIG. 21 shows glenoid components in place.
Figure 22:
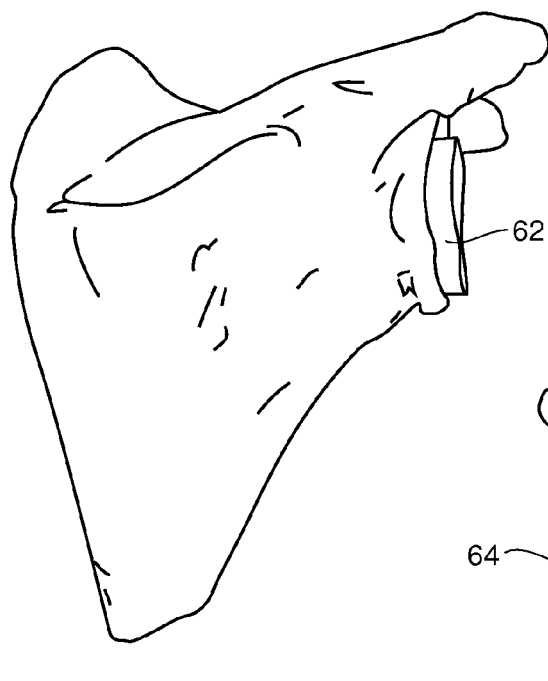
FIG. 22 shows glenoid components in place.
Figure 23:
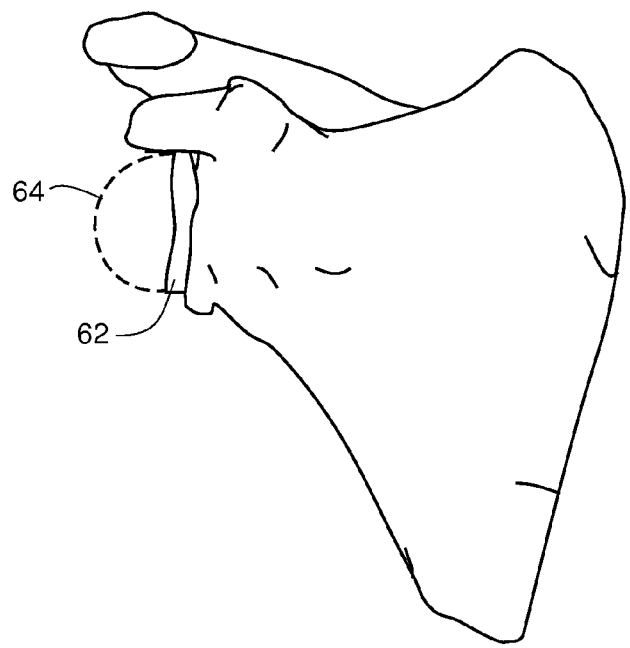
FIG. 23 shows glenoid components in place.

FIG. 21 through FIG. 23 should be considered together as they show the glenoid implant component 62 in place on the glenoid. Both a "normal" glenoid component 62 is shown as well as a "reverse" glenoid component 64 in dotted outline.

Humeral Component in Position

Figure 24:
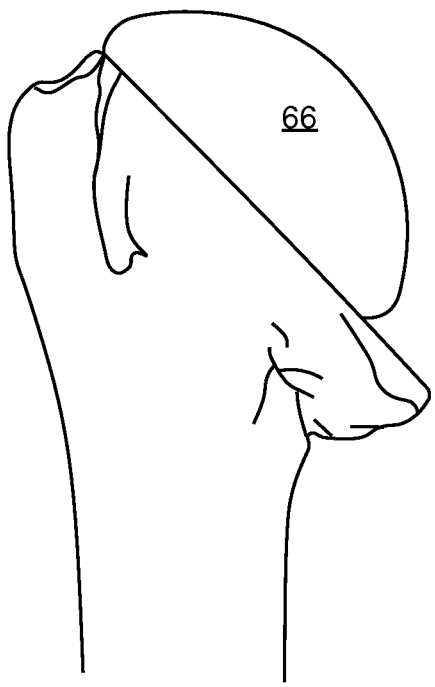
FIG. 24 shows humeral components in place.
Figure 25:
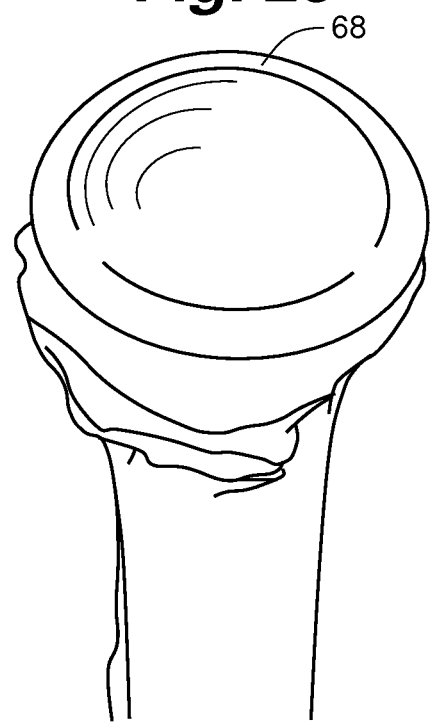
FIG. 25 shows humeral components in place.
Figure 26:
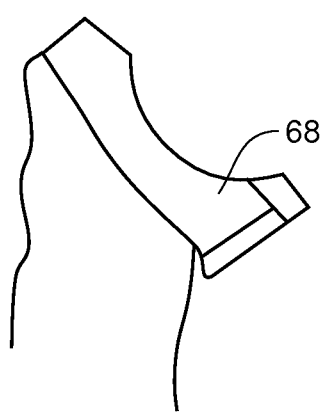
FIG. 26 shows humeral components in place.

FIG. 24 through FIG. 26 should be considered together as the show the "normal" humeral implant component 66 in place on the humerus. FIG. 26 and FIG. 25 depict a "reverse" humeral component 68 in place on the bone.

Overview of Instrument Creation and Use

Figure 27:
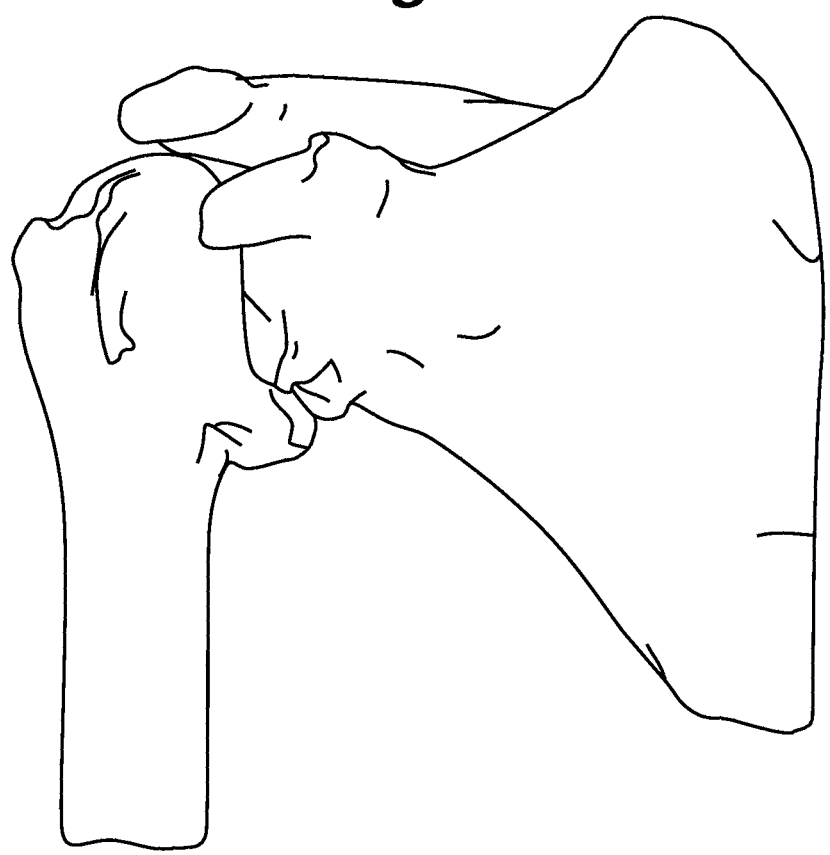
FIG. 27 shows a human shoulder joint.

FIG. 27 shows a human shoulder joint.

FIG. 28 shows a flowchart of the process beginning with the collection of patient data in process step 100. This data is used by process 120 to convert and display the native anatomy to a user. In process step 130 the image data is used with implant specific data to design the two instruments. In process step 140 instrumentation data is used to manufacture physical instruments. In process step 150 the surgeon uses the physical instruments to carry out the surgery.

Glenoid Component Instrument Creation Process

A software program Mimics® is used to take MRI or CT data and to create a 3-dimensional image of the glenoid and scapular spine that can be manipulated on the computer screen. The user defines three points, including a glenoid center point in the center of the glenoid articular surface, a junction point along the ridge of the scapular spine where the medial border and scapular spine meet, and an inferior point at the most distal end of the scapular spine. These three reference points depicted in FIG. 30 are used to define a coronal plane, which may be displayed on the image. A transverse plane orthogonal to the coronal plane is created through the glenoid center point and scapular spine junction point. Next a sagittal plane is created orthogonal to said two planes and centered on the center point of the glenoid as seen in FIG. 30. A reference anatomic axis may then be defined as the intersection of the transverse and sagittal planes. These steps may also be performed in a conventional software package such as "Pro/E" from PTC software company in Needham MA which is widely used to define parts in the CAD industry.

Figure 32:
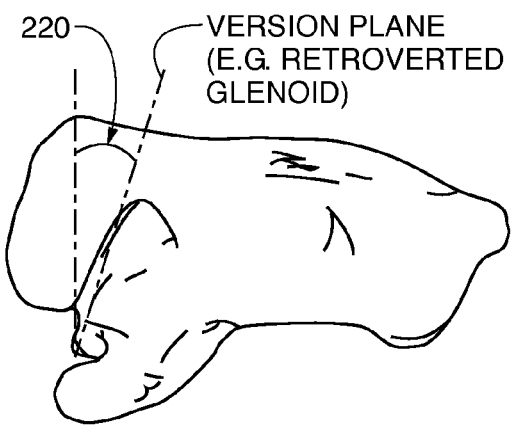
FIG. 32 shows anatomic geometry.

In order to reproduce the normal anatomic orientation of the glenoid after TSA, the ideal orientation of the glenoid component should have 4 degrees of superior inclination and 1 degree of retroversion. Therefore, the central peg or keel should achieve this orientation given adequate bone stock. In reverse total shoulder arthroplasty, the glenoid component should have 5 degrees of inferior inclination seen at reference numeral 200 in FIG. 29, close to neutral version, and slight inferior translation to minimize notching. This is seen in FIG. 29 and FIG. 32. Therefore, the inclination and version of the glenoid component will be referenced from the sagittal plane as defined. For example, the inclination plane can pass through an axis created by the intersection of the sagittal and transverse planes at 4 degrees of superior inclination as seen at reference numeral 210 in FIG. 29. A second axis can then pass through the coronal and inclination plane. The version plane can pass through said second axis at 1 degree of retroversion as seen at reference numeral 220 FIG. 32. At this point, the version plane will represent the proper orientation of the glenoid component; the glenoid component plane.

The alignment of the implant with the native bones is depicted in FIG. 31. At this point the operator and likely physician will review the position and size of the implant customized for this patient. With the implant location and size determined, Pro/E is used to create a template instrument that will be used to help align the glenoid component during the surgery. A portion of the glenoid component instrument is designed to conform to the native bone. The first surface of said portion of the glenoid component instrument has a surface that is 3D inverse of the native surface of the glenoid created via a Boolean subtraction operation where the native surface of the glenoid is subtracted from the template instrument. An approximately 1 mm gap between the bony surface of the glenoid and the inverse surface of the glenoid component instrument is added when using CT data to accommodate cartilage and/or slight errors in the reconstruction. This surface is created in Geomagic®. A second surface of said portion of the glenoid component instrument captures a bony surface close to but outside of the glenoid articular surface. Said second surface is an extending feature that is similarly created using a Boolean subtraction operation, and is used to help in the proper positioning of the instrument with respect to the bone. Said second surface wraps around the anterior aspect of the glenoid surface because it is easy to reference with a traditional delto-pectoral surgical approach, and can be used to lever the instrument over the glenoid. At least one and perhaps as many as three such features around the perimeter of the glenoid will be defined for the instrument depending largely upon the condition of the bone structure, its geometry, and surgical exposure.

The glenoid component instrument has a set of apertures that can function as windows to observe tissue and or as guide to direct cutting tools into the glenoid. For example, the instrument may carry a center hole for a drill bit to pass for a central peg designed glenoid component, or a slot to facilitate cutting a keel slot designed for a glenoid component. The orientation of the center aperture will be normal to glenoid component plane and be centered based on pre-operative plan. Peripheral holes in the instrument can be added to match any peripheral pegs/keels/screws or the like that the glenoid component may require. The peripheral holes will control the orientation of the glenoid component in rotation about the central axis for the glenoid component. The location of the holes or windows or slots will determine the rotation of the glenoid component. Next, the location of viewing slot(s) is defined for the instrument. These slots will be positioned so that they can be observed by the physician during the surgery and will communicate with the bony surface so that the presence or absence of a bony surface in the window helps verify the seating of the instrument. The remainder of the glenoid component instrument includes an extending handle that is directed away (usually anteriorly) from the axis of the peg/keel, as depicted in FIG. 15, in order to allow the drill to access the instrument.

For reverse total shoulder arthroplasty, a second glenoid component instrument can be used to target peripheral fixation screws for the glenoid component. After pre-operatively determining the depth of the reaming operation used to seat the glenoid component, the surgeon or engineer can pre-operatively determine the number, length, and alignment of said peripheral fixation screws. Said second glenoid component instrument will have a mating surface that is the 3D inverse of the reamed surface. The second instrument has a center hole in line with the central peg hole. In addition, peripheral holes in the second instrument will be in line with the pre-operatively planned screw locations. Drill taps will pass through said peripheral holes. The second instrument can also have as few as one mark on the visible (lateral) surface (e.g. a mark pointing superiorly) to aid in the rotational alignment of second instrument. During surgery, the surgeon can use electrocautery to mark the surface of the glenoid (e.g. a mark pointing superiorly). The second instrument's mark can now be aligned to the glenoid's surface mark. Viewing slots on the instrument will allow the surgeon to verify the seating of the instrument on the reamed bone. A handle extends laterally from second instrument but will not interfere with drill.

Bone modulus can be characterized from the Hounsfield unit obtained from CT scans. Bone with higher modulus is stronger, and would be ideal locations for peg/screw fixation. The surgeon or engineer can use this information to pre-operatively design the first and/or second instruments to direct the peg/screw into bone of higher modulus.

The process has created an instrument that can be used to define the location of a glenoid implant based upon an analysis of the native bone structure in conjunction with a representation of the glenoid implant.

Humeral Head Cutting Block Creation Process

Figure 33:
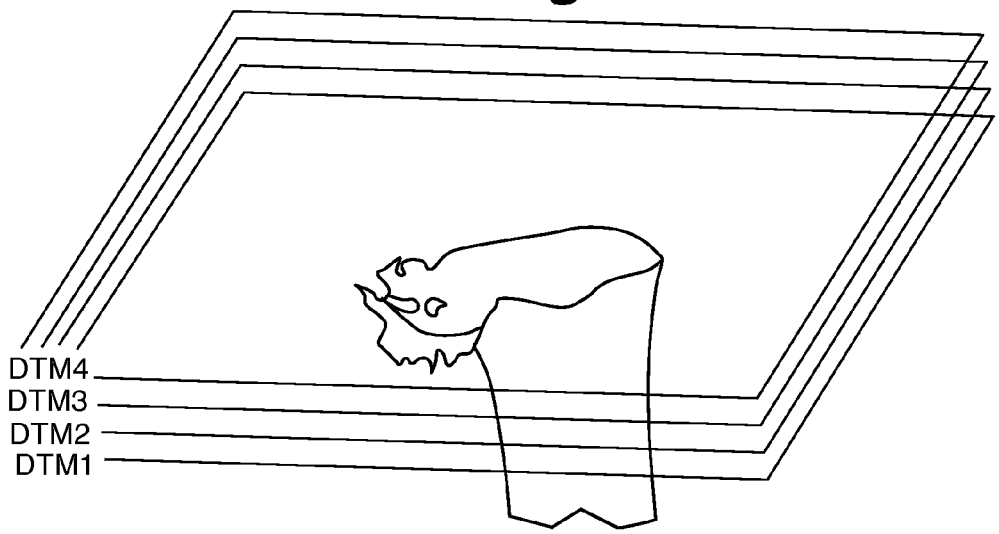
FIG. 33 shows part of a step in the process.
Figure 34:
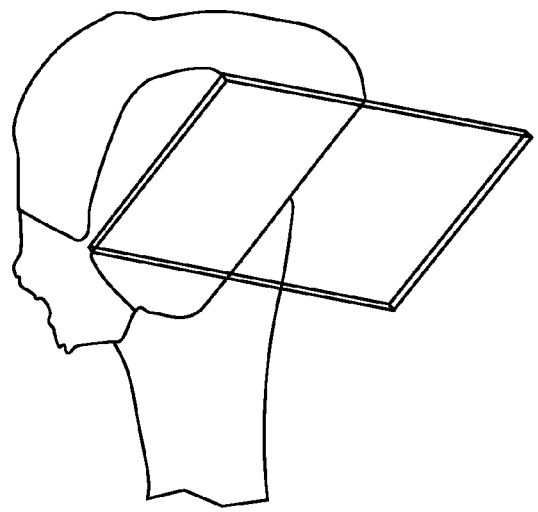
FIG. 34 shows part of a step in the process.

Similar to the glenoid component instrument, the humeral head cutting block utilizes MRI or CT data to determine the appropriate orientation and size of the orthopaedic component. For shoulder hemiarthroplasty and total shoulder arthroplasty, the position of the humeral component will be 20 degrees in retroversion. For reverse total shoulder arthroplasty, it will be closer to neutral. In order to properly correct the version of the humeral head, it is recommended that a MRI or CT scan of the elbow (same side) be taken as well. The diaphysis of the humerus will be approximated to be a cylinder with its long axis to be defined as the long axis of the humerus. Landmark points will be placed on the medial and lateral epicondyles of the distal humerus. A humeral coronal plane passes through said landmark points and is parallel to said long axis. The version of the humeral head will be offset from the coronal plane. If the elbow is not scanned, the calcar of the humerus can be used as a reference when determining version angle as depicted in FIG. 33. A calcar landmark point is identified. In this case, the version plane of the humeral component is defined as the plane that passes through said calcar point and the long axis of the humerus. Pre-operative sizing of the humeral head and humeral component can be performed. Humeral head resection and implant sizing performed pre-operatively on a left humerus.

Figure 20:
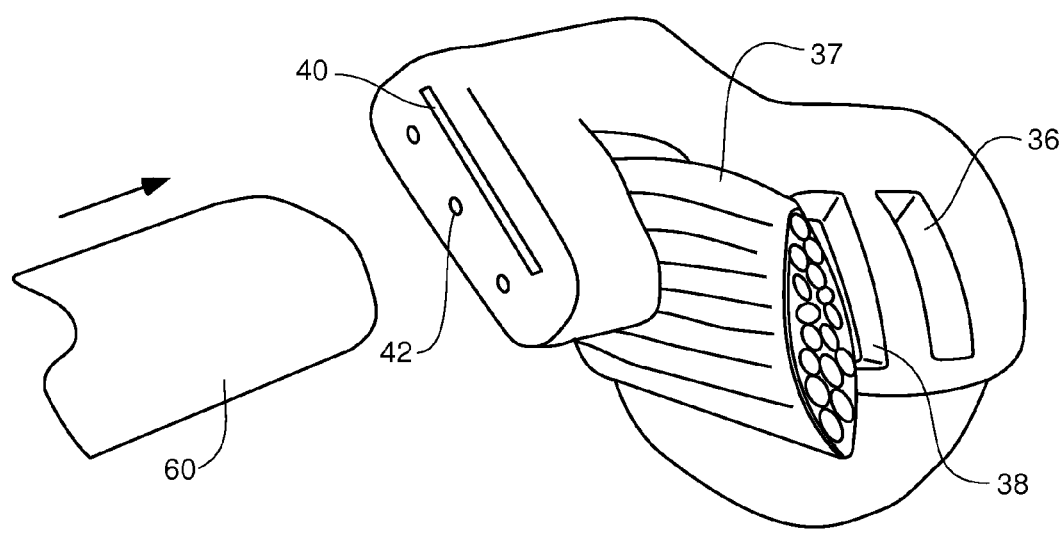
FIG. 20 shows the humeral cutting guide block in use against the humeral head.

The level of resection is built into the humeral head cutting block. Using MRI or CT data, this block engages with the humeral head by having a backside face that is a 3D inverse of the native humeral head created via a Boolean subtraction operation where the native surface of the humeral head is subtracted from a template block instrument. An approximately 1 mm gap between the bony surface of the humeral head and the inverse surface of the humeral head cutting block is added when using CT data to accommodate cartilage and/or slight errors in the reconstruction. Said block engages the superior-medial aspect of the head and has an additional feature that wraps around the lateral side of the lesser tubercle (subscapularis attachment sight) to additionally aid in the alignment of the block. The instrument has openings to allow the subscapularis and rotator cuff to pass without impingement as depicted in FIG. 20. The slot for the saw blade 40 is located approximately anterior to the humerus, and its cutting angle (approximately 45 degrees) is dependent on the implant system being used. Said slot has enough width to ensure that the blade remains parallel to the slot.

Other features include a minimum of two non-parallel pin holes for additional stability of the block to the proximal humerus. Said pin holes are located distal to the saw blade slot, and can accept pins screws or other fasteners. Viewing slots/portals on the block are used to visually ensure that the instrument is fully seated onto the humeral head. A targeting sight in line with the long axis of the humerus on the superior surface of the humeral head cutting block is used to target the humeral stem reamer.

The instruments will be steam sterilizable and biocompatible (e.g. DuraForm polyamide). Both the glenoid component instrument and the humeral head cutting block have been prototyped and manufactured. For the proper execution of these instruments during surgery, it is necessary to minimize the profile and volume of these instruments as much as possible, as the surgical exposure for these types of procedures are small. Modifications to these instruments continue to be made to make the operative procedure more efficient and accurate.

What is claimed is:

1. A patient specific surgical instrument for positioning the glenoid component of a shoulder implant said glenoid component having a keel or a plug component for fixing the glenoid component, a joint including a diseased native glenoid articular joint surface and an adjacent anterior glenoid fossa, said instrument comprising:
    an instrument body fabricated specifically to have a patient derived surface computed from image data of said diseased native glenoid articular joint surface creating a negative surface such that said instrument body has a surface that approximately matches and conforms to said diseased native glenoid joint surface;
    an index feature formed in the periphery of said instrument body and directly adjacent and contiguous with said instrument body, said index feature fabricated specifically to have a patient derived surface for engaging a portion of said adjacent anterior glenoid fossa, to position and locate said instrument body patient derived surface on said diseased native glenoid joint anatomy;
    at least one cutting guide through said instrument body to locate and direct cutting tools for aligning the keel or the plug component of the glenoid component for use in total shoulder arthroplasty in a pre-operatively planned orientation is less than or equal to 0° of version.

2. The patient specific instrument of claim 1 further including a handle coupled to said instrument body to facilitate instrument placement during surgery.

3. A patient specific instrument for facilitating the implant of a glenoid component of a total shoulder arthroplasty implant in a patient having a shoulder joint, the joint including a diseased native glenoid articular joint surface and an adjacent anterior glenoid fossa, said instrument comprising:
    an instrument body with an upper surface and a lower surface and a side wall;
    said lower surface being specifically shaped to form the inverse of a computer imaged diseased native glenoid joint articular surface of said patient;
    said instrument body having one or more apertures passing from said upper surface to said lower surface; said one or more apertures oriented relative to the diseased native glenoid joint to accept and direct a tool to prepare said diseased native glenoid articular surface for the implantation of a joint component accordingly to a patient specific pre-surgical plan; and
    an index surface feature continuous with and extending from said side wall, the index surface feature having a surface corresponding to the negative of a portion of the anterior aspect of said glenoid joint surface.

4. The patient specific instrument of claim 3 wherein the orientation and location of said index feature locates said aperture in a pre-operatively planned location, corresponding to component orientation of 1 degree of retroversion and 4 degrees of superior inclination.

5. The patient specific instrument of claim 3 wherein at least one of the one or more apertures has a rectangular shape and the tool is a cutting tool.

6. The patient specific instrument of claim 3 wherein at least one of the one or more apertures has a circular shape and the tool is a wire.

7. The patient specific instrument of claim 3 wherein at least one of the one or more apertures has a circular shape and the tool is a drill bit.

8. The patient specific instrument of claim 3 wherein at least one of the one or more apertures has a slot shape to facilitate cutting a keel slot designed for the glenoid component.

9. A patient specific instrument for facilitating the implant of a glenoid component of a reverse total shoulder arthroplasty implant in a patient having a shoulder joint, the joint including a diseased native glenoid articular joint surface and an adjacent anterior glenoid fossa, said instrument comprising:
    an instrument body with an upper surface and a lower surface and a side wall;
    said lower surface being the inverse of a three dimensional image of the diseased native glenoid joint articular surface of said patient;
    said instrument body having one or more apertures passing from said upper surface to said lower surface ,at least one of said one or more apertures provided in a pre-surgical planned position within the instrument body to form a center aperture to accept and orient tools used to prepare said diseased native glenoid articular surface for the implantation of a prosthetic joint component; and an index surface feature directly adjacent, continuous with and extending from the lower surface so as to at least partially engage with a portion of the anterior glenoid fossa of the diseased native glenoid.

10. The patient specific instrument of claim 9 wherein the orientation and location of said index feature locates said aperture in a pre-operatively planned location, corresponding to component orientation of 0 degrees of retroversion and 5 degrees of inferior inclination.

* * * * *